(12) United States Patent
Berinstein et al.

(10) Patent No.: US 8,802,383 B2
(45) Date of Patent: *Aug. 12, 2014

(54) MONOCLONAL ANTIBODIES AND USES THEREOF

(75) Inventors: Neil Berinstein, Toronto (CA); Devender Satsangi Singh Sandhu, Thornhill (CA); Corey Lovitt, Bolton (CA); Artur Pedyczak, Pickering (CA); Scott Gallichan, Burington (CA); Laszlo Radvanyi, Houston, TX (US)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,934

(22) Filed: May 16, 2012

(65) Prior Publication Data

US 2012/0295275 A1 Nov. 22, 2012

Related U.S. Application Data

(60) Continuation of application No. 12/836,299, filed on Jul. 14, 2010, now Pat. No. 8,361,706, which is a division of application No. 11/704,031, filed on Feb. 8, 2007, now Pat. No. 7,790,857.

(60) Provisional application No. 60/772,146, filed on Feb. 10, 2006.

(51) Int. Cl.
*G01N 33/574* (2006.01)
*G01N 33/53* (2006.01)
*C12Q 1/00* (2006.01)
*C07K 14/00* (2006.01)
*C07K 16/00* (2006.01)

(52) U.S. Cl.
USPC ............... 435/7.23; 435/7.1; 435/4; 530/350; 530/388.1

(58) Field of Classification Search
USPC .............................................. 435/4, 7.1, 7.23
See application file for complete search history.

(56) References Cited

U.S. PATENT DOCUMENTS

2011/0045502 A1* 2/2011 Berinstein et al. ........... 435/7.23

OTHER PUBLICATIONS

Harmsen and Haard (Appl Microbiol Biotechnol 2007, 77:13-22).*
Mariuzza et al. (Annu. Rev. Biophys. Biophys. Chem. 1987; 16: 139-159).*
Pietrantonio et al. (Anticancer Research, 2013, 33: 1257-1266).*
Chang et al. (Endocrine-Related Cancer, 2004, 11:815-822).*

* cited by examiner

*Primary Examiner* — Mark Halvorson
*Assistant Examiner* — Yan Xiao
(74) *Attorney, Agent, or Firm* — Patrick J. Halloran; Reza Yacoob

(57) ABSTRACT

The technology relates to monoclonal antibodies useful in the identification of cancer cells. In one embodiment, mAbs with specificity for tumor antigens are provided. In one embodiment, methods for treating cancer using mAbs are provided. In another embodiment, methods for detecting cancerous cells are provided. In another embodiment, kits for detecting cancerous cells are provided.

20 Claims, No Drawings

SEQUENCE LISTING

```
<160> NUMBER OF SEQ ID NOS: 6

<210> SEQ ID NO 1
<211> LENGTH: 22
<212> TYPE: PRT
<213> ORGANISM: Homo sapiens

<400> SEQUENCE: 1

Met Val Arg Lys Lys Asn Pro Pro Leu Arg Asn Val Ala Ser Glu Gly
1               5                   10                  15

Glu Gly Gln Ile Leu Glu
            20

<210> SEQ ID NO 2
<211> LENGTH: 22
<212> TYPE: PRT
<213> ORGANISM: Homo sapiens

<400> SEQUENCE: 2

Ser Pro Lys Ala Thr Glu Glu Thr Gly Gln Ala Gln Ser Gly Gln Ala
1               5                   10                  15

Asn Cys Gln Gly Leu Ser
            20
```

```
<210> SEQ ID NO 3
<211> LENGTH: 22
<212> TYPE: PRT
<213> ORGANISM: Homo sapiens

<400> SEQUENCE: 3

Val Ala Lys Pro Ser Glu Lys Asn Ser Asn Lys Ser Ile Pro Ala Leu
1               5                   10                  15

Gln Ser Ser Asp Ser Gly
            20

<210> SEQ ID NO 4
<211> LENGTH: 22
<212> TYPE: PRT
<213> ORGANISM: Homo sapiens

<400> SEQUENCE: 4

Asn His Leu Gln Gly Ser Asp Gly Gln Gln Ser Val Lys Glu Ser Lys
1               5                   10                  15

Glu His Ser Cys Thr Lys
            20

<210> SEQ ID NO 5
<211> LENGTH: 22
<212> TYPE: PRT
<213> ORGANISM: Homo sapiens

<400> SEQUENCE: 5

Asn Gly Glu Gln Ile Ile Arg Arg Arg Thr Arg Lys Arg Leu Asn Pro
1               5                   10                  15

Glu Ala Leu Gln Ala Glu
            20

<210> SEQ ID NO 6
<211> LENGTH: 23
<212> TYPE: PRT
<213> ORGANISM: Homo sapiens

<400> SEQUENCE: 6

Ala Asn Gly Ala Ser Lys Glu Lys Thr Lys Ala Pro Pro Asn Val Lys
1               5                   10                  15

Asn Glu Gly Pro Leu Asn Val
            20
```

MONOCLONAL ANTIBODIES AND USES THEREOF

RELATED APPLICATIONS

This application is a continuation application of U.S. Ser. No. 12/836,299 filed Jul. 14, 2010, now U.S. Pat. No. 8,361,706 which is a divisional application of U.S. Ser. No. 11/704,031 filed Feb. 8, 2007, now U.S. Pat. No. 7,790,857 B2, which claims priority to U.S. Ser. No. 60/772,146 filed Feb. 10, 2006.

FIELD OF THE INVENTION

The technology relates to monoclonal antibodies useful in the identification of cancer cells.

BACKGROUND OF THE INVENTION

Monoclonal antibodies have proven useful in the diagnosis and treatment of diseases such as cancer. Those active in the field of disease prevention and diagnosis understand that for certain conditions, additional reagents are required to improve the prevention and/or treatment of such diseases. One such area is oncology. Despite recent advances in the field, there is a need for additional highly specific diagnostic reagents useful in diagnosing cancer. The technology described herein provides such reagents, as shown below.

SUMMARY OF THE INVENTION

The technology relates to monoclonal antibodies useful in the identification of cancer cells. In one embodiment, mAbs with specificity for tumor antigens are provided. In one embodiment, methods for treating cancer using mAbs are provided. In another embodiment, methods for detecting cancerous cells are provided. In another embodiment, kits for detecting cancerous cells are provided.

DETAILED DESCRIPTION

The technology described herein relates to antibodies for use in identifying cells expressing the BFA4 protein as well as diagnosing, treating and/or preventing one or more diseases associated with the existence of such cells. The tem "antibody" or "antibodies" includes whole or fragmented antibodies in unpurified or partially purified form (i.e., hybridoma supernatant, ascites, polyclonal antisera) or in purified form. A "purified" antibody is one that is separated from at least about 50% of the proteins with which it is initially found (i.e., as part of a hybridoma supernatant or ascites preparation). Preferably, a purified antibody is separated from at least about 60%, 75%, 90%, or 95% of the proteins with which it is initially found. Suitable derivatives may include fragments (i.e., Fab, $Fab_2$ or single chain antibodies (Fv for example)), as are known in the art. The antibodies may be of any suitable origin or form including, for example, murine (i.e., produced by murine hybridoma cells), or expressed as humanized antibodies, chimeric antibodies, human antibodies, and the like.

Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No. 1*, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147 (1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (i.e., −20° C. or −70° C.), in lyophilized form, or under normal refrigeration conditions (i.e., 4° C.). When stored in liquid form, it is preferred that a suitable buffer such as Tris-buffered saline (TBS) or phosphate buffered saline (PBS) is utilized.

To identify potential antigens useful in producing monoclonal antibodies reactive against cancer cells, differential gene expression profiling of tumor and normal tissues was performed using DNA microarrays, followed by validation of gene expression at the protein level and elucidation of T-cell reactivity against predicted peptide epitopes. Gene profiling using microarrays was performed with 54 breast tumor specimens obtained immediately following surgery, including ductal carcinoma in situ, invasive ductal carcinoma, and liver and lung metastases. In each case, the gene expression patterns in the tumours were compared to expression profiles obtained from over 100 normal tissues and cell types in order to identify genes over-expressed specifically in breast cancer. This screening approach led to the detection of a number of over-expressed, breast tumour-specific genes. One of the most highly over-expressed genes ("BFA4") was found to be identical to a GATA family transcriptional regulator shown to associate with a rare autosomal dominant genetic disorder called trichorhinophalangeal syndrome type 1 (TRPS-1) (Momeni, P. et al. *Nat Genet* 24, 71-4 (2000); Malik, et al. *Mol Cell Biol* 22, 8592-600 (2002); Ludecke, et al. *Am J Hum Genet* 68, 81-91 (2001); Kaiser, et al. *Eur J Hum Genet* 12, 121-6 (2004)). BFA4 was found to be expressed in greater than 90% of breast cancers at the protein level. Antibodies reactive therewith, and in particular monoclonal antibodies (mAbs) reactive therewith, are described herein.

One such mAb is termed "8D11", and a murine hybridoma producing 8D11 was deposited on Jul. 12, 2005 with the American Type Culture Collection (ATCC), 10801 University Blvd., Manassas, Va. 20110-2209, U.S.A. under the provisions of the Budapest Treaty for the International Recognition of the Deposit of Microorganism for the Purposes of Patent Procedure, and accorded Patent Deposit Designation PTA-6852. A hybridoma producing a second antibody showing reactivity with the BFA4 protein is termed "8A1" was similarly deposited with the ATCC on Jul. 12, 2005 and accorded Patent Deposit Designation PTA-6853. Other antibodies, including polyclonal antisera or preparations of isolated antibodies contained therein, for example, are also provided herein.

In certain embodiments, preparations of 8D11 and/or 8A1 are provided. Such preparations may include unpurified antibody as found in a hybridoma supernatants or ascites preparation, partially purified preparations, or purified preparations. Thus, provided herein are antibody preparations containing 8D11 and/or 8A1 purified to about 50%, 60%, 75%, 90%, or 95% purity. Typically, such preparations include a buffer such as phosphate- or tris-buffered saline (PBS or TRIS, respectively). Also provided are derivatives of 8D11 and/or 8A1 including fragments (Fab, $Fab_2$ or single chain antibodies (Fv for example)), humanized antibodies, chimeric antibodies, human antibodies, and the like. The genes encoding the variable and hypervariable segments of 8D11 and/or 8A1 may also be isolated from the hybridomas expressing the same cloned into expression vectors to produce certain antibody preparations (i.e., humanized antibodies). Methods for producing such preparations are well-known in the art.

The skilled artisan has many suitable techniques for using the antibodies described herein to identify biological samples containing proteins that bind thereto. For instance, the antibodies may be utilized to isolate BFA4 protein using, for example, immunoprecipitation or other capture-type assay. This well-known technique is performed by attaching the antibody to a solid support or chromatographic material (i.e., a bead coated with Protein A, Protein G and/or Protein L). The bound antibody is then introduced into a solution either containing or believed to contain the BFA4 protein. BFA4 protein then binds to the antibody and non-binding materials are washed away under conditions in which the BFA4 protein remains bound to the antibody. The bound protein may then be separated from the antibody and analyzed as desired. Similar methods for isolating a protein using an antibody are well-known in the art.

The antibodies may also be utilized to detect BFA4 protein within a biological sample. For instance, the antibodies may be used in assays such as, for example, flow cytometric analysis, ELISA, immunoblotting (i.e., western blot), in situ detection, immunocytochemistry, and/or immunhistochemistry. Methods of carrying out such assays are well-known in the art.

To assist the skilled artisan in using 8D11 and 8A1, the same may be provided in kit format. A kit including 8D11 and/or 8A1 and optionally other components necessary for using the antibodies to detect cells expressing BFA4 is provided. The antibodies of the kit may be provided in any suitable form, including frozen, lyophilized, or in a pharmaceutically acceptable buffer such as TBS or PBS. The kit may also include other reagents required for utilization of the antibodies in vitro or in vivo such as buffers (i.e., TBS, PBS), blocking agents (solutions including nonfat dry milk, normal sera, Tween-20 Detergent, BSA, or casein), and/or detection reagents (i.e., goat anti-mouse IgG biotin, streptavidin-HRP conjugates, allophycocyanin, B-phycoerythrin, R-phycoerythrin, peroxidase, fluors (i.e., DyLight, Cy3, Cy5, FITC, HiLyte Fluor 555, HiLyte Fluor 647), and/or staining kits (i.e., ABC Staining Kit, Pierce)). The kits may also include other reagents and/or instructions for using the antibodies in commonly utilized assays described above such as, for example, flow cytometric analysis, ELISA, immunoblotting (i.e., western blot), in situ detection, immunocytochemistry, immunhistochemistry.

In one embodiment, the kit provides 8D11 and/or 8A1 in purified form. In another embodiment, 8D11 and/or 8A1 are provided in biotinylated form either alone or along with an avidin-conjugated detection reagent (i.e., antibody). In another embodiment, the kit includes a fluorescently labelled 8D11 and/or 8A1 which may be used to directly detect BFA4 protein. Buffers and the like required for using any of these systems are well-known in the art and may be prepared by the end-user or provided as a component of the kit. The kit may also include a solid support containing positive- and negative-control protein and/or tissue-samples. For example, kits for performing spotting or western blot-type assays may include control cell or tissue lysates for use in SDS-PAGE or nylon or other membranes containing pre-fixed control samples with additional space for experimental samples. Kits for visualization of BFA4 in cells on slides may include pre-formatted slides containing control cell or tissue samples with additional space for experimental samples.

8D11 and/or 8A1 and/or derivatives thereof may also be incorporated into compositions of the invention for use in vitro or in vivo. The antibodies or derivatives thereof may also be conjugated to functional moieties such as cytotoxic drugs or toxins, or active fragments thereof such as diphtheria A chain, exotoxin A chain, ricin A chain, abrin A chain, curcin, crotin, phenomycin, enomycin, among others. Functional moieties may also include radiochemicals.

8D11 and 8A1 and/or derivatives thereof may be used in assays to determine the presence of a disease state in a patient, to predict prognosis, or to determine the effectiveness of a chemotherapeutic or other treatment regimen. Expression profile assays, performed as described herein or as is otherwise known in the art, may be used to determine the relative level of expression of BFA4. The level of expression may then be correlated with base (i.e., control) levels to determine whether a particular disease is present within the patient, the patient's prognosis, or whether a particular treatment regimen is effective. For example, if the patient is being treated with a particular chemotherapeutic regimen, a decreased level of expression of an immunogenic target in the patient's tissues (i.e., in peripheral blood, breast tissue biopsy) may indicate the regimen is decreasing the cancer load in that host. Similarly, if the level of expression is increasing, this may indicate the regimen is not having the desired effect and another therapeutic modality may be selected.

It is also possible to use the antibodies described herein as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

The antibodies described herein may be prepared as injectable preparation, such as in suspension in a non-toxic parenterally acceptable diluent or solvent. Suitable vehicles and solvents that may be utilized include water, Ringer's solution, and isotonic sodium chloride solution, TBS and PBS, among others. In certain applications, the antibodies are suitable for use in vitro. In other applications, the antibodies are suitable for use in vivo. The preparations suitable for use in either case are well-known in the art and will vary depending on the particular application.

All references cited herein are hereby incorporated by reference. A better understanding of the present invention and of its many advantages will be had from the following examples, given by way of illustration.

EXAMPLES

Example 1

Generation and Characterization of Polyclonal and Monoclonal Antibodies

A. Polyclonal Antibodies

Polyclonal antibodies were generated against 22-mer or 23-mer peptides conjugated to keyhole limpet hemocyanin (KLH). The peptide sequences were as follows:

```
                        (CLP2589; SEQ ID NO: 1)
KLH-MVRKKNPPLRNVASEGEGQILE, (CLP2590; SEQ ID NO: 2)
KLH-SPKATEETGQAQSGQANCQGLS, (CLP25691; SEQ ID NO: 3)
KLH-VAKPSEKNSNKSIPALQSSDSG, (CLP2592; SEQ ID NO: 4)
KLH-NHLQGSDGQQ SVKESKEHSCTK, (CLP2593; SEQ ID NO: 5)
KLH-NGEQIIRRRTRKRLNPEALQAE,
and
                        (CLP2594; SEQ ID NO: 6)
KLH-ANGASKEKTKAPPNVKNEGPLNV.
```

White New Zealand rabbits (Harlan) were immunized intramuscularly with 100 μg of peptide emulsified in CFA and boosted on days 15, and 28 with peptide and IFA. Final antibody titres from bleeds taken on day 57 ranged from 1:40,000 to 1:320,000. Polyclonal antibodies (pAb) were generated against a series of 22-mer peptides in the BFA4 sequence. One of these pAb, designated 2589, recognized a specific band in BT474 and MDA-MB 453 breast tumour cells migrating at 200-220 kDa following SDS-PAGE and Western blotting. The BFA4 protein also migrated with the same molecular weight in lysates from NYVAC-BFA4-infected Vero cells (data not shown).

B. Monoclonal Antibodies

Monoclonal antibodies (mAbs) were generated against a 54 kDa His-tagged NH$_2$ amino terminal recombinant protein of BFA4 (BFA4-N54). The recombinant protein was cloned into pGEX4T1-6His is plasmid, expressed in E. coli, and purified from bacterial lysates by column chromatography on NiNTA columns. Monoclonal antibodies were produced at ImmunoPrecise Antibodies Ltd. (Victoria, BC, Canada). Briefly, BFA4-N54 protein (50 μg) was emulsified in CFA and injected subcutaneously into Balb/c mice. Hybridomas were generated after 3 boosts and screened in ELISA. Out of 21 clones, two clones (designated 8D11 and 8A1) were found to exhibit optimal ELISA and immunoblot reactivity against recombinant the recombinant protein and in lysates of BFA4-expressing cell lines. Hybridoma culture supernatants were purified using Protein G chromatography. The migration of the BFA4 protein in SDS-PAGE was further confirmed using immunoblot analysis with two monoclonal antibodies (mAb) designated 8D11 and 8A1. A single 200-220 kDa band was found in BT474 and MDA-MB453 cell lysates with no detectable expression in COS cells used as a specificity control.

To further confirm the specificity of the mAbs, breast cancer cell lines (BT474, MDA-MB 453, and MDA-MB-231) and control cell lines (COS and HeLa) were grown on glass coverslips in 24-well plates and washed with PBS. The cells were then fixed with 3% paraformaldehyde in PBS, washed three times with PBS, 10 mM NH$_4$Cl and permeabilized in PBS, 0.1% saponin (PBS/sapo) for 10 min. The cells were stained with primary antibodies followed by Alexa-488-coupled secondary antibodies diluted in PBS/sapo/HS. The cells were counterstained with 0.05% Evans blue. Stained slides were analyzed with a Zeiss Axioplan epifluorescence microscope or a Zeiss LSM confocal fluorescence microscope equipped with an appropriate set of filters. Nuclear expression of BFA4 was observed in BT474, MDA-MB453, and MDA-MB231 breast tumour lines. No detectable expression was found in HeLa or COS cells used as controls as well as with secondary antibody alone.

C. Immunohistochemical Studies

To ascertain the utility of the mAbs for staining tissue sections, formalin-fixed paraffin-embedded breast cancer biopsy specimens were obtained from the Henrietta Banting Breast Cancer Repository of Sunnybrook and Women's College Health Sciences Center (SWCHSC) in Toronto, Ontario. Fifty tumour sections consisting of DCIS, invasive ductal and lobular carcinoma and mixed DCIS and invasive carcinoma were stained with 8D11 and 8A1. Antigen retrieval was performed by heat-treating the sections in a pressure cooker at 120° C. for 2.5 min in BORG buffer, pH9.5 followed by a 20-30 min cooling period without pressure after blocking endogenous peroxidase. The slides were washed in Tris-HCl, pH 7.6 and incubated with a 1:50 dilution of affinity-purified 8D11 or 8A1 mAb. After three washes in Tris buffer, the slides were treated with Dako Envision Plus anti-mouse-HRP antibody for 30 min and washed again three times in Tris-HCl buffer. The slides were developed with DAB solution for ten minutes followed by counterstaining with hematoxylin, dehydration, clearing, and mounting. Arrays of normal tissues (MaxArray, Zymed Laboratories) were also stained using the same staining protocol. Slides were scored according to the percentage of cells and the percentage of tumour specimens staining positive. The intensity of staining in the sections was scored as low, intermediate or high. A parallel set of sections from the same tumour specimens were also stained for ER1, PR, and HER2-neu according to previously published methods (Patient, et al. *Curr. Opin. Genet. Dev.* 12, 416-22 (2002)).

1. Expression in Normal Tissues

A striking result of the IHC analysis was the virtual absence of BFA4 expression in normal tissues that were stained. Representative photomicrographs showed a lack of any detectable BFA4 expression in normal liver, lung, colon, kidney, normal breast, and skin. Similar results were obtained with samples from heart, stomach, spleen, liver, pancreas, small intestine, peripheral nerves, cerebral cortex, cerebellum, thyroid gland, pituitary, adrenal gland, uterus, cervix, salivary gland, and bone marrow. Some weak staining was found in the cytoplasm in a few cerebral cortical cells of brain using the 8D11. However, no staining was found with 8A1 suggesting that the weak staining of these few cerebral cortex cells was non-specific. In both invasive carcinoma and DCIS patient samples, some low to intermediate level of BFA4 expression was seen in a proportion of the normal breast epithelial cells from these patients. The significance of this is not known, but may indicate an abnormality in these cells in breast cancer patients.

2. Expression in Tumor Tissues

It was observed that BFA4-stained tumour sections showing strong nuclear staining in invasive ductal carcinomas, DCIS, mixed invasive ductal carcinoma and DCIS. Expression of BFA4 in a RLN metastasis sample was also observed. The distribution of BFA4 staining in terms of percentage nuclei stained was also determined for the 50 rumours analyzed. The majority of samples expressed BFA4 in greater than 75% of the cells in the tumour mass. In invasive ductal carcinomas samples (n=40), 90% of the samples had 75% or more of the cells stained with 8D11. Similar results were obtained using 8A1, with 84% of the samples having 75% or more of the cells staining positive. The relationship between ER-1 and HER-2/neu status of the tumours and BFA4 expression for cases of invasive carcinoma and DCIS and found that BFA4 was highly expressed in ER-1$^+$ and ER-1$^-$, as well as HER2/neu$^+$ and HER2/neu$^-$ tumours. Based on this IHC analysis, it was concluded that expression of the BFA4 protein is highly tumour specific and has a comprehensive expression throughout the patient population (over 90% positive) in both early and late stages of breast cancer.

Expression of BFA4 was also determined in samples of lung carcinoma, B cell lymphoma, T cell lymphoma, colon carcinoma, pancreatic and biliary carcinomas, hepatocelluar carcinoma, renal cell carcinoma, and ovarian carcinoma. 8A1 and 8D11 stained a minority of B cell lymphomas and pancreatic/biliary carcinomas. 8D11 demonstrated cytoplasmic staining in 9 of 18 colon carcinoma samples, 4 of 9 hepatocellular carcinoma samples, and 3 of 17 renal cell carcinoma samples. Nineteen of 20 ovarian carcinoma samples were positive for nuclear staining and sixteen of 20 ovarian carcinoma samples were positive for cytoplasmic staining using 8D11. Sixteen of 20 ovarian carcinoma samples were positive for nuclear staining using 8A.

As shown herein, 8D11 and 8A1 may be used alone or in combination with one another to detect cancer cells of various origins. These mAbs may also be combined with other reagents to provide kits for identifying the expression of BFA4.

Example 2

Kit for Identifying Cells Expressing BFA4/TRPS-1

A kit including 8D11 and/or 8A1 and optionally other components necessary for using the antibodies to detect cells expressing BFA4 is provided. The antibody may be provided in any suitable form, including frozen, lyophilized, or in a suitable buffer such as phosphate-buffered saline (PBS). In one embodiment, the 8A1 and/or 8D11 are provided individually in purified form. In such instances, the user may choose to affix a detectable label (i.e., biotin, FITC) to the antibody. In another embodiment, the kit includes 8D11 or 8A1 with a detectable label (i.e., biotin) attached. For example, in one embodiment, the kit includes biotinylated 8A1 and/or 8D11 and an avidin-conjugated detection reagent (i.e., secondary antibody). In another embodiment, the kit includes a fluorescently labelled 8D11 and/or 8A1. Buffers and the like as well as detection systems required for using any of these systems are well-known in the art and may be prepared and utilized by the end-user or provided as a component of the kit. For example, The kit may also include a solid support containing positive- and negative-control protein and/or tissue samples. For example, kits for performing spotting or western blot-type assays may include control cell or tissue lysates for use in SDS-PAGE or membranes containing pre-fixed control samples with additional space for experimental samples. Kits for visualization of BFA4 in cells on slides may include pre-formatted slides containing control cell or tissue samples with additional space for experimental samples.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. A method for determining the effectiveness of a treatment regimen for treating cancer by detecting the expression level of an antigen in a biological sample of a patient before and after treatment, the antigen being reactive with the monoclonal antibody 8D11 produced by the mouse hybridoma having ATCC Designation No. PTA-6852 and/or a derivative thereof selected from the group consisting of an $F_{ab}$, $F_{ab2}$, single chain antibody, $F_v$, humanized antibody, and a chimeric antibody, and/or the monoclonal antibody 8A1 produced by the mouse hybridoma having ATCC Designation No. PTA-6853 and/or a derivative thereof selected from the group consisting of an $F_{ab}$, $F_{ab2}$, single chain antibody, $F_v$, humanized antibody, and a chimeric antibody, the method comprising:

determining the level of expression of the antigen in the biological sample obtained before treatment by detecting the binding of the monoclonal antibody 8D11 and/or a derivative thereof and/or the monoclonal antibody 8A1 and/or a derivative thereof to components of the biological sample;

determining the level of expression of the antigen in the biological sample obtained after treatment by detecting the binding of the monoclonal antibody 8D11 and/or a derivative thereof and/or the monoclonal antibody 8A1 and/or a derivative thereof to components of the biological sample;

wherein:

an increase in expression of the antigen after treatment indicates the treatment is not effective; and, an decrease in expression of the antigen after treatment indicates the treatment is effective.

2. The method of claim 1 wherein the treatment regimen includes a chemotherapeutic drug.

3. The method of claim 1 wherein the biological sample is a cell or tissue of the patient.

4. The method of claim 3 wherein the patient is a human being.

5. The method of claim 1 wherein the monoclonal antibody is monoclonal antibody 8D11 produced by the mouse hybridoma having ATCC Designation No. PTA-6852 and/or a derivative thereof.

6. The method of claim 5 wherein the treatment regimen includes a chemotherapeutic drug.

7. The method of claim 5 wherein the biological sample is a cell or tissue of the patient.

8. The method of claim 7 wherein the patient is a human being.

9. The method of claim 1 wherein the monoclonal antibody is monoclonal antibody 8D11 produced by the mouse hybridoma having ATCC Designation No. PTA-6852.

10. The method of claim 9 wherein the treatment regimen includes a chemotherapeutic drug.

11. The method of claim 9 wherein the biological sample is a cell or tissue of the patient.

12. The method of claim 11 wherein the patient is a human being.

13. The method of claim 1 wherein the monoclonal antibody is monoclonal antibody 8A1 produced by the mouse hybridoma having ATCC Designation No. PTA-6853 and/or a derivative thereof.

14. The method of claim 13 wherein the treatment regimen includes a chemotherapeutic drug.

15. The method of claim 13 wherein the biological sample is a cell or tissue of the patient.

16. The method of claim 15 wherein the patient is a human being.

17. The method of claim 1 wherein the monoclonal antibody is monoclonal antibody 8A1 produced by the mouse hybridoma having ATCC Designation No. PTA-6853.

18. The method of claim 17 wherein the treatment regimen includes a chemotherapeutic drug.

19. The method of claim 17 wherein the biological sample is a cell or tissue of the patient.

20. The method of claim 19 wherein the patient is a human being.

* * * * *